(12) United States Patent
Silver et al.

(10) Patent No.: US 6,328,931 B1
(45) Date of Patent: *Dec. 11, 2001

(54) ANALYTE COLLECTION AND ASSAYING ASSEMBLY

(75) Inventors: Lawrence Stanley Silver, Hauppauge; Michael Juliano, East Setauket, both of NY (US)

(73) Assignee: International Food Protection, Inc., Bayport, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/510,954

(22) Filed: Feb. 22, 2000

Related U.S. Application Data

(63) Continuation-in-part of application No. 09/370,306, filed on Aug. 9, 1999, which is a continuation-in-part of application No. 09/228,330, filed on Jan. 11, 1999, now Pat. No. 6,197,254.

(51) Int. Cl.[7] .................................................. G01N 21/76
(52) U.S. Cl. ............................ 422/52; 422/56; 422/58; 422/59; 422/60; 422/61; 422/82.08; 422/102; 422/940; 436/165; 436/169; 436/170; 436/172; 435/288.7; 250/361 C
(58) Field of Search ................................ 422/52, 55, 56, 422/58–61, 82.08, 99, 100, 102, 939, 940; 436/164, 165, 169, 170, 172, 180; 435/288.7; 250/361 C

(56) References Cited

U.S. PATENT DOCUMENTS

| | | |
|---|---|---|
| 4,672,039 | 6/1987 | Lundblom ............................ 435/291 |
| 5,188,965 | 2/1993 | Wannlund ............................ 436/165 |
| 5,565,360 | 10/1996 | Lapota et al. ......................... 435/286 |
| 5,624,810 * | 4/1997 | Miller et al. ............................. 435/8 |
| 5,783,399 | 7/1998 | Childs et al. ......................... 435/7.2 |
| 5,811,251 | 9/1998 | Hirose et al. ............................. 435/8 |
| 5,827,675 * | 10/1998 | Skiffington et al. ...................... 435/8 |
| 5,905,029 * | 5/1999 | Andreotti et al. ........................ 435/8 |
| 5,980,828 * | 11/1999 | McClintock et al. .................. 422/58 |
| 6,043,047 * | 3/2000 | Foote et al. ............................. 435/21 |
| 6,140,136 * | 10/2000 | Lee ...................................... 436/518 |
| 6,197,254 * | 3/2001 | Silver et al. ............................ 422/52 |

FOREIGN PATENT DOCUMENTS

| | | |
|---|---|---|
| 0038134 B1 | 7/1985 | (EP) . |
| 0717840 B1 | 11/1998 | (EP) . |
| 98/49544 * | 11/1998 | (WO) . |

* cited by examiner

*Primary Examiner*—Maureen M. Wallenhorst
(74) *Attorney, Agent, or Firm*—Island Patent

(57) ABSTRACT

Swabbing and assaying structures, and selected methods of use, enable a test surface to be swabbed, and subsequently facilitate a quantitative determination of the quantities of analyte collected from the test surface. The swabbing structures include a pre-wetted swabbing pad having a first surface for contacting and suitably swabbing the test surface to collect the analyte. Dried reagents that are impregnated within or upon a porous pad are then brought into pressure contact with the swabbing pad, within a suitable light-tight environment. If sufficient analyte was collected by the swabbing of the test surface, an assaying reaction will commence that produces detectable and quantifiable low level luminescent emissions.

19 Claims, 12 Drawing Sheets

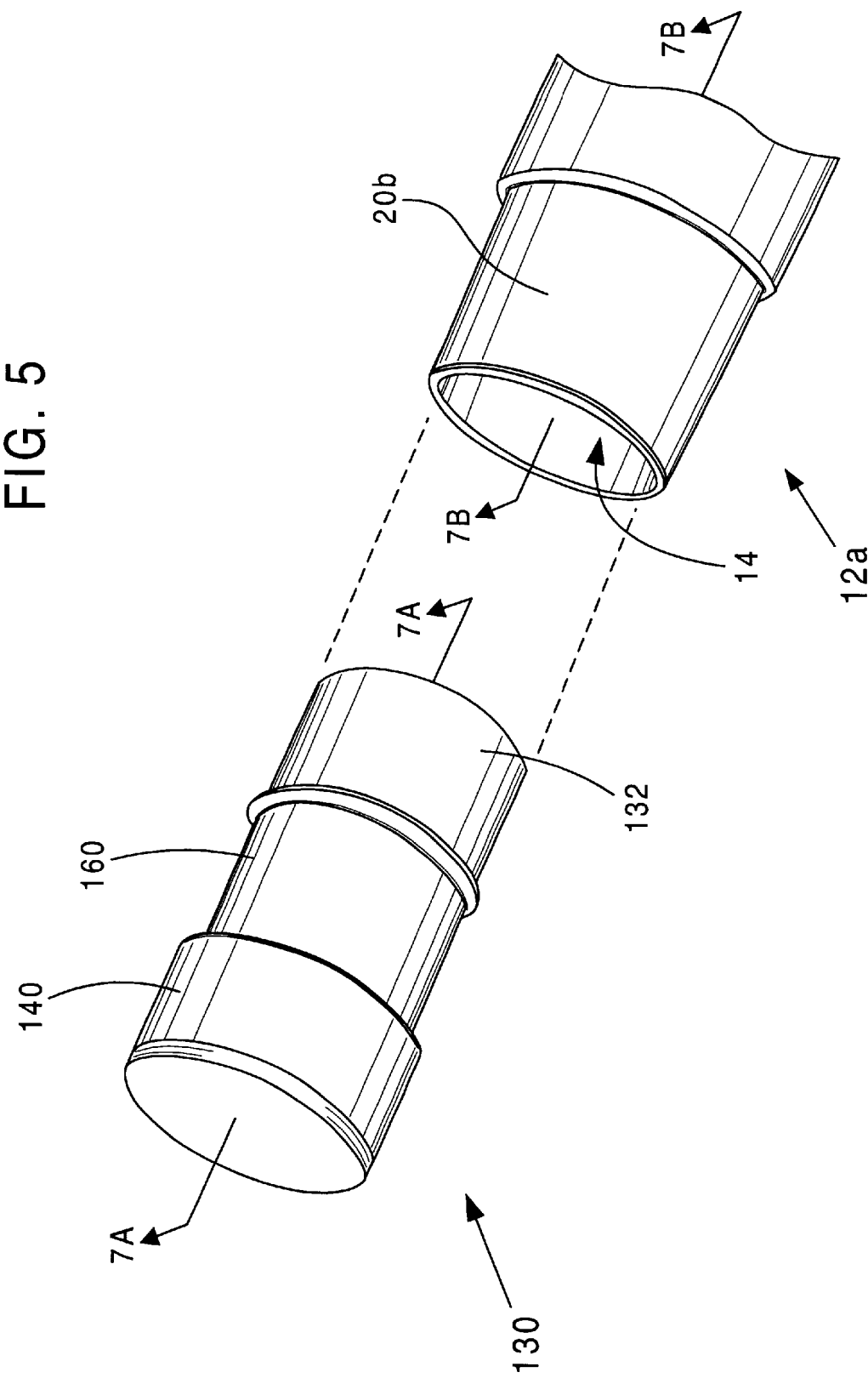

US 6,328,931 B1

ANALYTE COLLECTION AND ASSAYING ASSEMBLY

CROSS REFERENCE TO RELATED APPLICATIONS

The subject matter provided herein represents a continuation-in-part of application Ser. No. 09/370,306 filed on Aug. 9, 1999, which is a continuation-in-part of application Ser. No. 09/228,330 filed on Jan. 11, 1999, now U.S. Pat. No. 6,197,254, issued on Mar. 6, 2001, each of which is hereby incorporated by reference.

TECHNICAL FIELD

The present invention relates generally to swabbing and related structures useful for assaying purposes. More particularly, the invention relates swabbing and related structures for collecting analyte from a test surface and conducting a self-contained assay in a light-tight environment to efficiently detect and quantify low level luminescent emissions, which are proportional in intensity to the volume of analyte collected from the test surface.

BACKGROUND ART

A number of techniques and arrangements have been proposed that employ 'luciferase-luciferin reactions' to assay and quantify a volume of analyte. As is well known, luciferase-luciferin reactions involve the measurement of adenosine triphosphate (ATP), a material central to metabolism in virtually all living cells. Since ATP is necessary for all living organisms to function, it serves as an excellent marker to indicate the presence of living matter (e.g., bacterial and or other microbial matter). Accordingly, if one can ascertain (with a reasonable accuracy) a quantity of ATP present in a sample or specimen, either through direct or indirect measurement, one may make a determination of the quantity of microbes, microbial matter, or more generally the amount of 'analyte' present. A most preferred indirect method of measuring and quantifying a volume of analyte is by determining the levels of ATP present by employing a luciferase-luciferin assaying reaction. A properly conducted luciferase-luciferin reaction will produce detectable and measurable levels of luminescent emissions—even with relatively small quantities of analyte (e.g., down to 1 femtomole, or so). However, it must be understood that the level of luminescent emissions generated by such assaying reactions may be quite low. For example, such intensity levels of emissions may be as low as a fraction of a pico-watt. The measurement of emission levels this low necessitates sensitive, efficient, and accurate detecting and measuring systems that include low noise and often specialized components.

Assaying arrangements that employ bioluminescent (ATP) assaying reactions to produce low levels of luminescent emissions also require a means to collect a specimen or sample. Once a sample has been collected (say with a cotton tipped swab), the sample is assayed by exposure to suitable enzymes and reagents to cause the luminescent emissions-producing reaction to occur. The art provides many examples of luminometer apparatus that are employable in a lab or testing facility to measure emissions of such an assaying reaction. However, these assaying arrangements are not provided in self-contained and highly portable architectures structured for the "efficient detecting" of low-levels of luminescent emissions in accordance with the present invention. Therefore, such systems have not been especially usable in the field, for example, if a cleanliness or hygiene inspection is being conducted in a hospital operating room or in a restaurant's kitchen. In addition, known swabbing structures and associated assaying arrangements do not provide simple, self-contained, and efficient structures to collect a sample of analyte, initiate an assaying reaction (in a light-tight environment), and subsequently sense and quantify the low levels of luminescent emissions produced by the reaction.

Accordingly, skilled persons will recognize the need for improved low level, self-contained and highly portable assaying apparatus, and associated (efficient) swabbing arrangements and structures. A most preferred swabbing structure would enable specimens to be collected, provide a suitable light-tight assaying environment (i.e., enclosure), include required chemical and biological materials to initiate the assaying reaction, and further enable or support the efficient quantifying of the low level luminescent emissions produced by the assaying reaction. If properly quantified, the actual (relative) intensity levels of the low-level luminescent emissions may be employed to determine a measure of the volume of microbial matter that was collected by the swabbing of the test surface. A full understanding of the present invention, including an understanding of a number of capabilities, characteristics, and associated novel features, will result from a careful review of the description and figures of the embodiments provided herein. Attention is called to the fact, however, that the drawings and descriptions are illustrative only. Variations and alternate embodiments are contemplated as being part of the invention, limited only by the scope of the appended claims.

SUMMARY OF THE INVENTION

In accordance with the present invention, swabbing structures and methods of use, are provided for collecting a volume of analyte from a test surface, and supporting a quantitative determination of the relative volume collected. A detector cap assembly providing an internal light-tight environment for conducting a self-contained assay of analyte collected from a test surface includes a first portion and a second portion. The first portion is structured with a first porous pad fixed thereto. The first portion is removably fixable to a detector head assembly of a luminometer to enable the efficient detecting and quantifying of low level luminescent emissions emitted, at least in part, from the first porous pad. The second portion is structured with a second porous pad suitably fixed thereto. The second portion is specifically configured to be removably fixed to the first portion to establish the light-tight environment. The light-tight environment houses the first porous pad and the second porous pad to enable the detection of the low level luminescent emissions free of any incident ambient light reaching either the first and second porous pads. Importantly, the first portion and the second portion are structured to enable a user to bring the first porous pad (fixed to the first portion) into pressure contact with the second porous pad (fixed to the second portion) within the light-tight environment. The pressure contacting possibly causing an assay reaction producing low level luminescent emissions that may be detectable and quantifiable by a suitable, preferably hand-holdable and self-contained luminometer.

The detector cap assembly may be embodied with the first porous pad of the first portion provided as a swabbing pad, or alternately a reagent holding or impregnated porous pad. Accordingly, the second porous pad would be provided to compliment the first porous pad. For example, if the first porous pad is provided as a reagent impregnated porous pad, then the second porous pad would be provided as a pre-wetted swabbing pad arranged to swab the test surface when separated from the second portion.

The invention further discloses preferred methods for swabbing a test surface in order to collect and quantitatively indicate the presence of an analyte. The methods commence with the swabbing of the test surface with a pre-wetted swabbing pad. A first surface of the swabbing pad is suitably shaped and configured for contacting the test surface to collect available analyte. Next, the first surface of the swabbing pad is brought into pressure contact with suitable dried reagents of another porous pad in a light-tight environment, possibly causing a detectable low level luminescent reaction (if sufficient analyte has been collected).

BRIEF DESCRIPTION OF THE DRAWINGS

In the drawings, like elements are assigned like reference numerals. The drawings are not necessarily to scale, with the emphasis instead placed upon the principles of the present invention. Additionally, each of the embodiments depicted are but one of a number of possible arrangements utilizing the fundamental concepts of the invention. The drawings are briefly described as follows:

FIG. 5 illustrates another embodiment of a detector cap assembly and a detector head assembly of a suitable luminometer.

PARTIAL LIST OF REFERENCE NUMERALS

Figure 1:
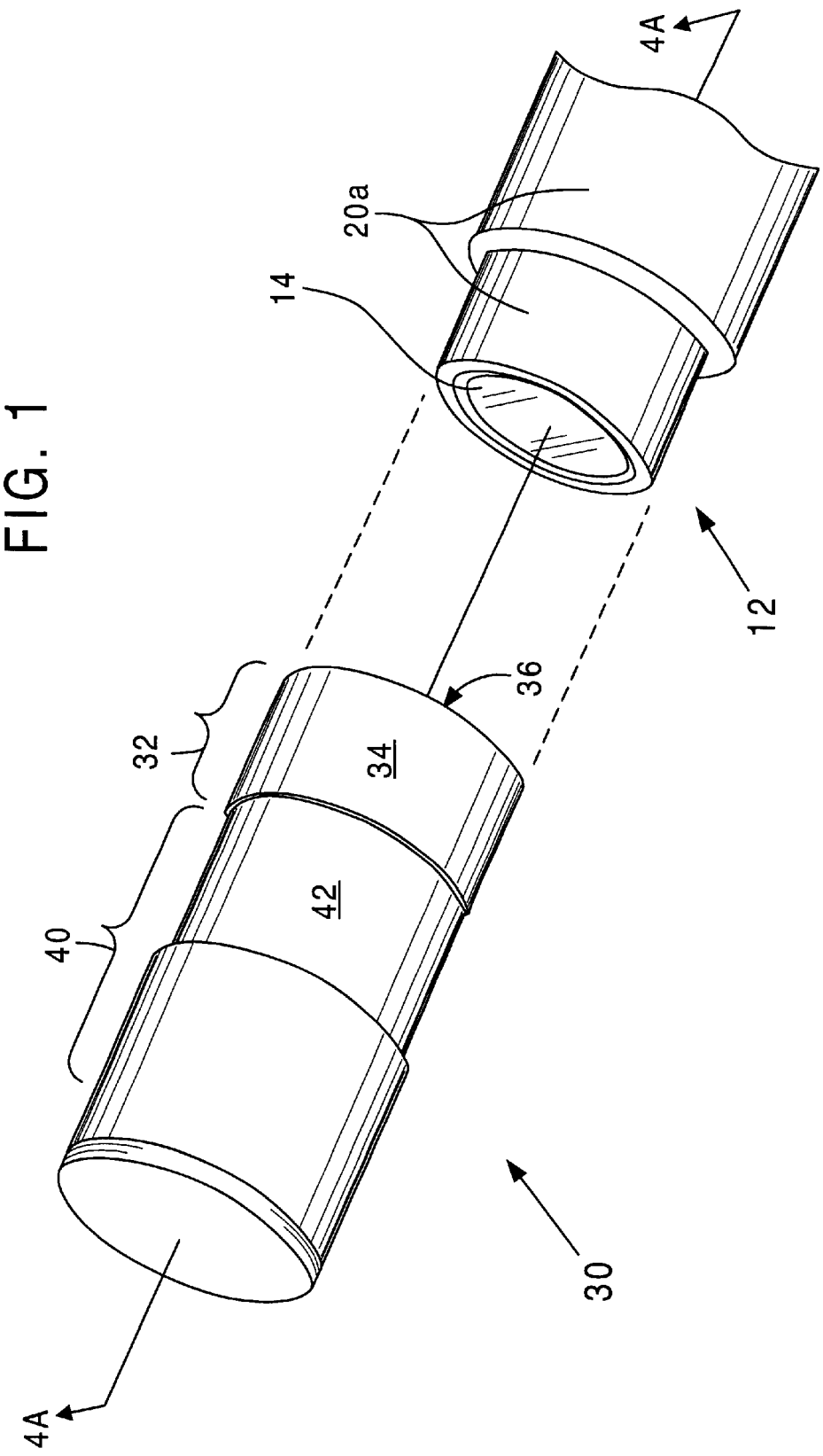
FIG. 1 illustrates a perspective view of an embodiment of a detector cap assembly and a detector head assembly of a suitable luminometer in accordance with the present invention.

12—detector head assembly
14—transparent or optical window
20a,20b—detector head housing
30—detector cap assembly
32—first portion (of detector cap assembly 30)
34—wall structure of first portion
34a—first opening of first portion
34b—second opening of first portion
36—internal cavity of first portion
40—second portion (of detector cap assembly 30)
42—wall structure of second portion
42a—first end of second portion
42b—second end of second portion
46—outer surface of wall structure 42'
46a—threaded portion of outer surface
48—internal chamber of second portion
52—opening to internal chamber of the second portion
54—swabbing pad
54a—first (swabbing) surface (of swabbing pad 54)
54b—second surface (of swabbing pad 54)
56—support and reading pad
56a—first surface (of reading pad 56)
56b—second surface (of reading pad 56)
64—movable structure
64a—surface of movable structure
68—porous pad
70—moisture barrier, or sealing means
70a—support ring for first barrier
78, 78a—second barrier
79—(small) pocket
80—cap-like portion
82—wall structure of cap-like portion
82a—first (open) end of cap-like portion
82b—second (closed) end of cap-like portion
84—top surface of cap-like portion
86—interior surface of wall structure
86a—threaded portion of interior surface of wall structure
124—photodetector or semiconductor photodiode
124a—second semiconductor photodiode (if included)
130—detector cap assembly (an alternate embodiment)
132—first portion (of alternate embodiment)
134—wall structure of 132
140—second portion (of alternate embodiment)
142—wall structure (of second portion)
144—internal cavity of 140
160—spacer
180—light-tight environment

DETAILED DESCRIPTION OF EMBODIMENTS OF THE INVENTION

It is important to establish the definition of a number of terms and expressions that will be used throughout this disclosure. The term 'luminometer', which is used extensively through out this disclosure, defines a means to measure low levels of luminescent emissions. Importantly, a preferred luminometer for use with the present invention is embodied to provide a very portable, hand holdable or belt/waist supported, self-contained instrument. Such an instrument could be used 'on-site' to measure low level luminescent emissions produced when an assay is being conducted. The expression 'low level luminescent emissions', and similar expressions, are to be assumed to indicate levels of emissions typified by, for example, a luciferase-luciferin type of bioluminescent assaying reaction. Such an assaying reaction, as well as other known reactions, may produce a correspondingly low level emission, say for example, as low as one-hundredth of a pico-watt. Further, such emissions may preferably be within the visible light spectrum. The term 'analyte' is to be understood to encompass small microbes including, but not limited to, bacteria, viruses, other chemical moieties, and the like. Further, 'analyte' may be assumed to be singular or plural, as appropriate for the context in which it is used. The term 'wall structure' will be used primarily to refer to side walls of several portions of a detector cap assembly of the present invention. It should be understood, however, that the term wall structure may be extended to include a top or end wall of a respective item being described, as determined by the context in which the term (wall structure) is applied. Two other very important terms, which will also be used extensively in this disclosure, are 'first portion' and 'second portion'. The term first portion may be assumed to indicate a portion of a detector cap assembly of the invention, or an equivalent structure, which is closest to, and preferably removably fixable to the detector head assembly of a suitable luminometer. Similarly, the second portion may be assumed to indicate another portion of the detector cap assembly that is structured to mate to, or be removably fixed to, the first portion so as to, among other things, complete an interior chamber or cavity that houses porous pads of the present invention in a light-tight environment. The expression 'light-tight environment', and similarly 'light-tight manner', and equivalents, are intended to indicate that the structures of a first portion and a second portion will mate (i.e. be removably fixable to each other) such that ambient light is shielded or blocked so that only luminescent emissions emitted from one or more porous pads (and associated internal structures) are incident upon a photo-detection means provided by the luminometer. Other important terms and definitions will be provided, as they are needed, to properly and fully define the present invention and its associated novel characteristics and features.

Referring now to FIG. 1, there is illustrated therein an embodiment of a detector cap assembly 30 and a detector head assembly 12. The detector head assembly, which represents a portion of a preferably hand-holdable self-contained luminometer, may include a transparent window 14, or an equivalent structure. The transparent window 14 provides a portal through which low level luminescent emissions may pass to be detected and quantified. Most preferably, the quantified (i.e., measured) luminescent emissions would be indicative of the relative volume of analyte being assayed in accordance with the invention. Situated just behind the transparent window 14 is a suitable 'photo-detection means', such as a closely placed semiconductor photo-diode. It should be noted that the detector head assembly 12 may be housed within a detector head housing 20a portion of a suitable housing. However, many suitable arrangements may be provided to house the detector head assembly 12 of the present invention. For example, another preferred and equivalent structural arrangement may be provided having the transparent window 14 and the photo-detection means recessed within a housing 20b, which will be fully discussed when referring to FIGS. 5 through 7C. As such, a detector head assembly 12, which is a male-type structure, may be converted to an equivalent arrangement possibly having a 'detector receptacle' or 'detector well', which may be configured to provide a female-type of structure. Accordingly, it may be noted that the term 'detector head assembly' is to be broadly defined to include protruding, surface type, or more recessed assemblies and structures having a suitable detecting element situated proximate to the source of luminescent emissions to enable the efficient detecting of the emissions.

Turning again to FIG. 1, there is depicted therein an embodiment of a detector cap assembly 30 of the present invention. The detector cap assembly 30 is comprised of a first portion 32 and a second portion 40. The first portion 32 is configured having a wall structure 34 forming, at least in part, an internal cavity 36. As implied in FIGS. 1 and 2, and explicitly shown FIG. 4A, the wall structure 34 of the first portion 32, which may be provided with a substantially cylindrical form (as illustrated), or other suitable shapes, defines a first opening 34a and a second opening 34b. In order to restrict ambient light from being incident upon porous pads of the invention (including the swabbing pad 54) during assaying activities, the wall structures of the first portion 32 and second portion 40, as well as portions of a housing of the luminometer and possibly other structures, must be opaque and suitably structured to provide the required light-tight environment. This will be discussed in further detail below.

Figure 3:
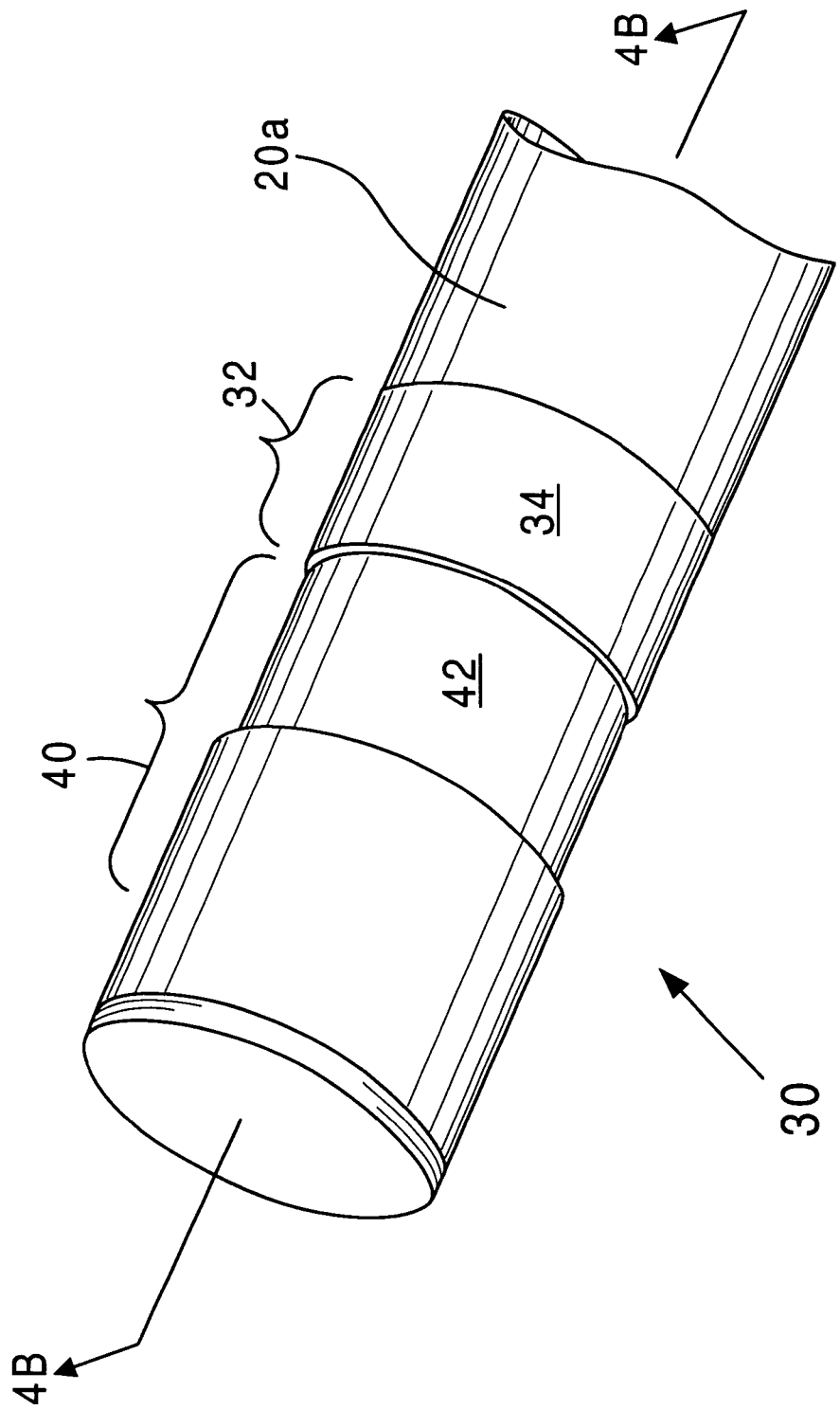
FIG. 3 depicts the detector cap assembly of FIGS. 1 and 2, reassembled, housing a first and a second porous pad and related structures in an interior light-tight environment.
Figure 4A:
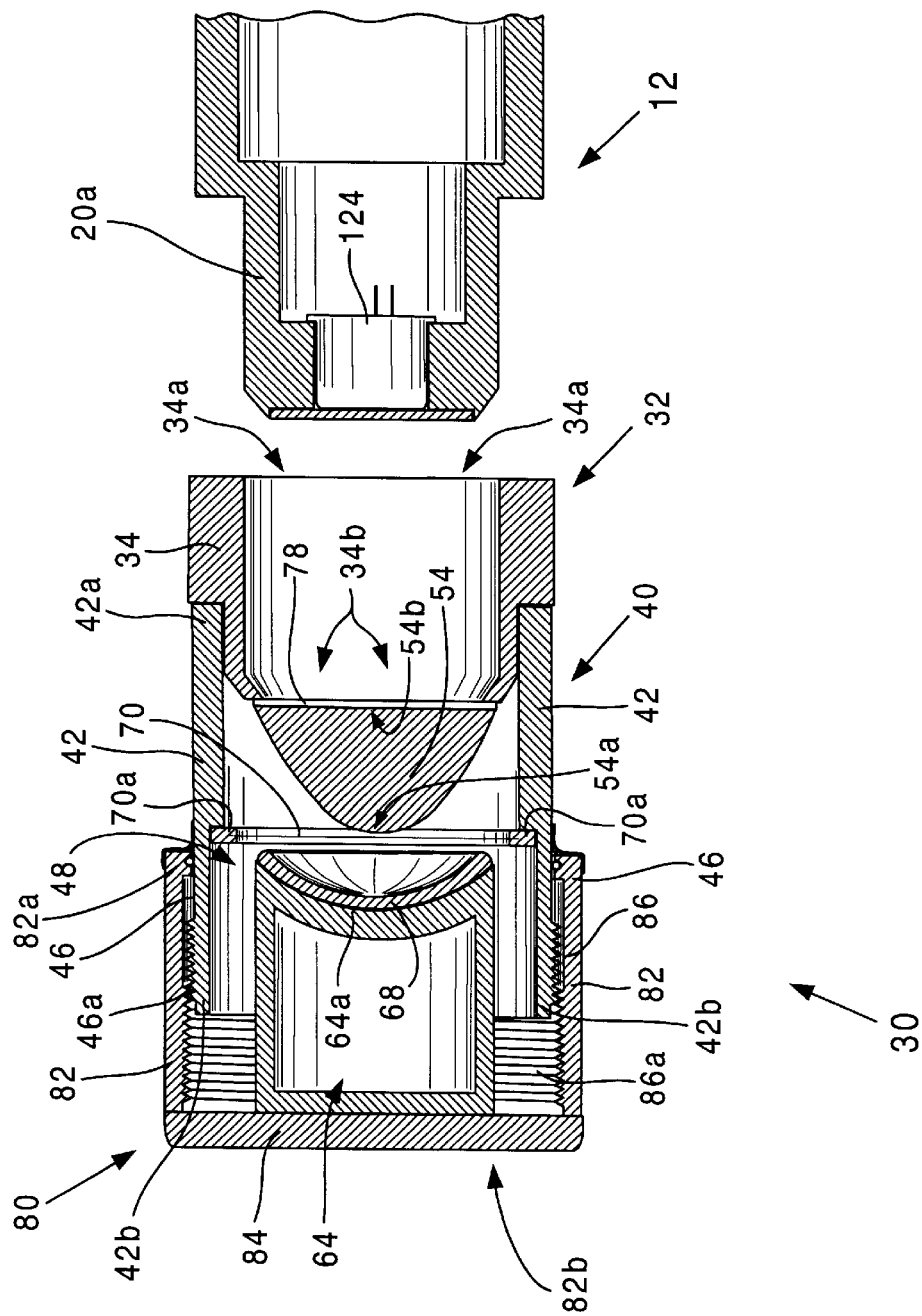
FIGS. 4A and 4B provide sectional side views of a first embodiment of a detector cap assembly of the present invention taken along the lines 4A—4A of FIG. 1 and the lines 4B—4B of FIG. 3, respectively.
Figure 4B:
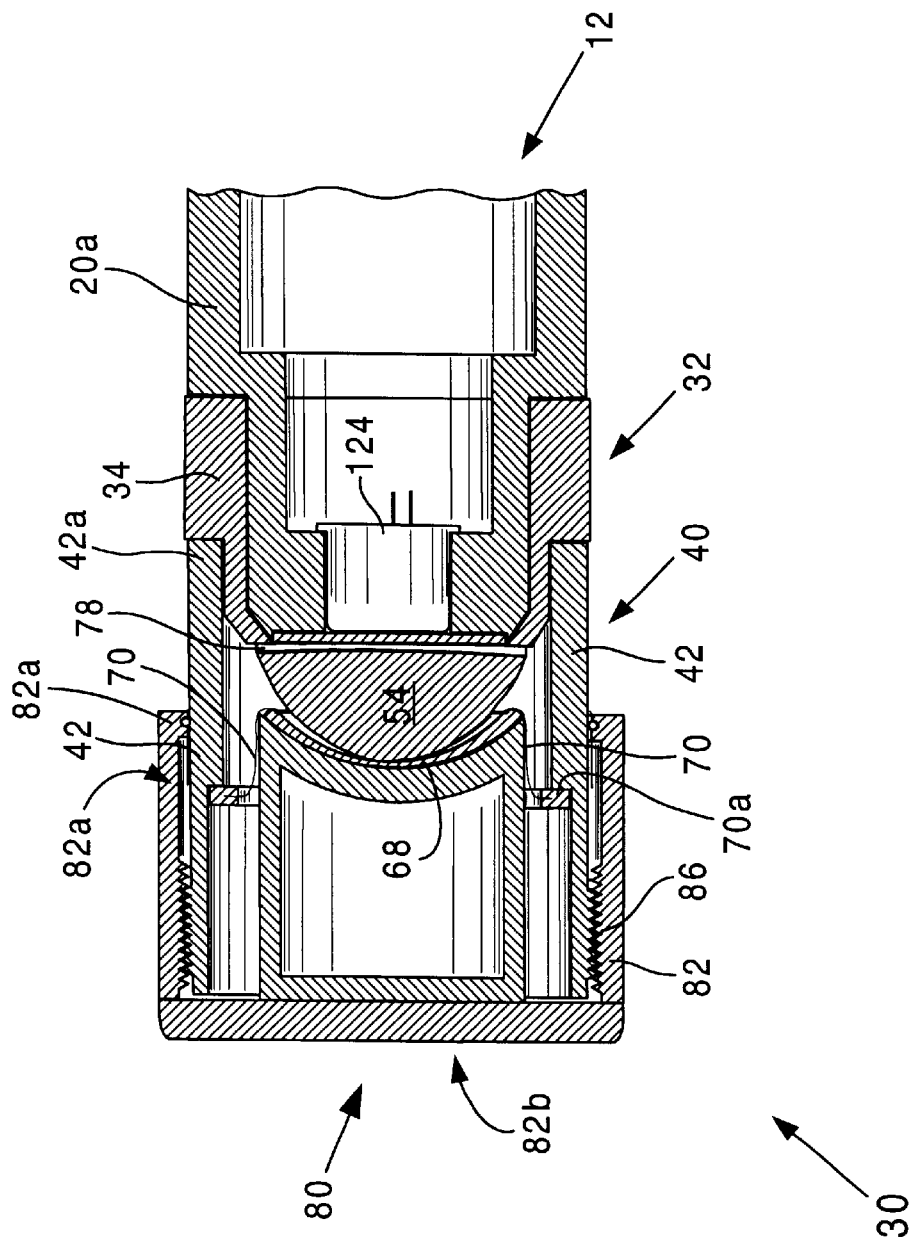

The first opening 34a and wall structure 34 of the first portion 32 are structured to enable the first portion 32 to be removably fixed over the detector head assembly 12 in a light-tight manner (see FIGS. 3 and 4B). As discussed above, the expression 'light-tight manner' is intended to indicate that the first portion 32 will mate to, and be removably fixable to, the detector head assembly 12 so as to only enable luminescent emissions passing through the second opening 34b of the first portion 32 to be incident upon a photo-detection means (situated behind the transparent window 14). In a preferred embodiment the first portion 32 will suitably install over (in a removably fixed fashion) the detector head assembly 12 such that at least a portion of the detector head assembly substantially fills the cavity 36 of the first portion 32. This arrangement will position the transparent window 14 of the detector head assembly 12 (as clearly shown in FIG. 4B) in close proximity to the second opening 34b of the first portion 32. Accordingly, this structure will minimize the distance between the photo-detection means and one or more included porous pads, to enable the 'efficient detecting' of the low level luminescent emissions emitted, at least in part, from the porous pads. This arrangement, wherein said distance is minimized, enables the low level luminescent emissions in accordance with the present invention to be readily and efficiently detected when generated an assaying reaction that is occurring on, within, or adjacent to one or more included porous pads. This specific aspect of the invention will be discussed in greater detail below.

Figure 2:
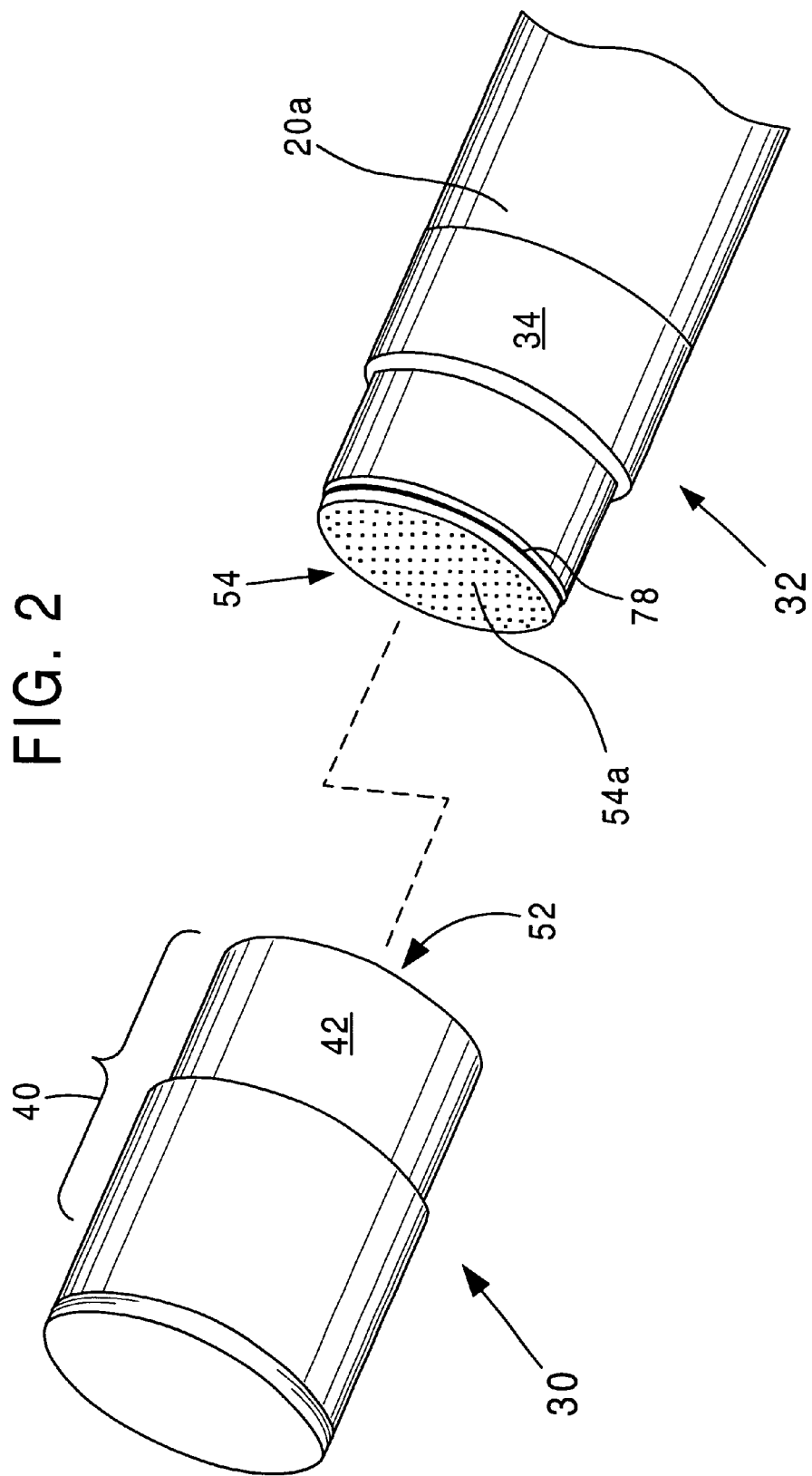
FIG. 2 provides a perspective view of the detector cap assembly of FIG. 1 with a first portion installed over the detector head assembly of a luminometer, and ready to be used for swabbing and analyte collection.

Referring again to FIG. 1, it may be assumed that the detector cap assembly 30 may have been removed from a sealed, possible sterile, packaging arrangement (not explicitly shown). Once removed from the packaging arrangement, the detector cap assembly 30 may be installed over (or into) a suitable detector head assembly in the light-tight manner (as illustrated if FIG. 3). Next, as shown in FIG. 2, the second portion 40 is separated from the first portion 32. A first porous pad, which when considering the embodiments of FIGS. 1 through 4b will be designated 'swabbing pad 54', is now exposed and available for swabbing of a selected test surface to collect analyte (to be assayed) upon the first surface 54a. When considering the embodiments of the swabbing pad 54 of the invention, such pads may be provided as a substantially flattened, pre-wetted "bibulous" and porous material, as depicted in FIG. 2. As can be seen, swabbing pad 54 is fixed to the first portion 32 of the detector cap assembly 30 and arranged to substantially cover the second opening 34b thereof. It must however be noted that the swabbing pad 54 may also be provided in a large variety of shapes, as can be seen in FIGS. 2, 4A, 7A, etc. As shown therein, a first surface 54a of the depicted (porous) swabbing pads 54 may not be flat. Indeed, when it is desired to swab and collect analyte from a crevice or along a curved, angled, or folded surface, the swabbing pad 54 may be most preferably structured having a shape similar to that illustrated in FIGS. 4A or 9. Importantly, as shown, the swabbing pad 54 is most preferably structured with a substantially flattened second surface 54b, which is ideally positioned superposed over and essentially abutting the window 14 of the detector head assembly 12 (when the first portion 32 is removably fixed over the detector head assembly 12 in the light-tight manner). After one or more selected test surfaces have been swabbed to collect analyte, the second portion 40 is re-installed over the first portion 32, as depicted in FIG. 3. Since the porous swabbing pad 54 is now covered by the second portion 40 in a light-tight environment, ambient light is no longer incident upon swabbing pad 54 (as well as other items now contained in the light-tight environment).

Turning again to FIGS. 4A and 4B, there are illustrated therein sectional views that are consistent with the embodiment illustrated in FIGS. 1, 2 and 3, and as such are representative of one possible internal structure that may be provided for this embodiment. As depicted, the second portion 40 is configured to house a movable structure 64 within a chamber 48 (as best seen in FIG. 4A). The movable structure 64 of this embodiment may be embodied having a substantially curved or concaved surface 64a, as illustrated, that is oriented proximate to, yet retracted from, the first surface 54a of the swabbing pad 54. The movable structure 64 is also configured to be movable between a first retracted position, wherein the movable structure 64 is contained within the chamber 48 (as illustrated in FIG. 4A), and a second deployed position (as illustrated in FIG. 4b). A porous pad 68, which may be termed 'a second porous pad' of the present embodiment, is fixed to and arranged to substantially cover a surface 64a of the movable structure 64. As such, the porous pad 68 may be said to be 'fixed to the second portion', or alternately, 'suitably fixed to the second portion', as illustrated.

In the embodiments of the detector cap assembly 30 shown in FIGS. 1 through 4B, the (second) porous pad 68 is preferably impregnated with suitable dried reagents that are activated by wetting when brought into pressure contact with a first porous pad, such as provided by a pre-wetted swabbing pad 54. It should be noted that the terms 'pressure contact' and 'pressure contacting' may be assumed to indicate that a porous pad (e.g., second porous pad 68) is brought into contact with another porous pad (e.g., first porous swabbing pad 54) with a sufficient pressure to enable the wetness of the swabbing pad 54 to wet and activate dried reagents that impregnate the porous pad 68. Skilled individuals will understand that the reagents will then dissolve and be drawn, at least in part) from the porous pad 68 to the swabbing pad 54. In a possibly most preferred embodiment of the invention of FIGS. 1 through 4B, when sufficient amounts of analyte (say a volume in the range of 10 to 100 microliters) are collected upon the swabbing pad 54, and sufficient luciferase-luciferin dried reagents are impregnated within the porous pad 68, a detectable luciferase-luciferin reaction will occur. This reaction, which may be termed an 'assaying reaction' having associated therewith assaying activities, may be assumed to produce low level luminescent emissions. It should be noted that the expression "possibly resulting in an assaying reaction producing detectable low level luminescent emissions" is intended to indicate that an assaying reaction will occur at a sufficient intensity, if analyte (e.g., microbial matter) is present in a sufficient volume on one or more porous pads of the invention. Conversely, if a sufficient volume of analyte is not present, the assaying reaction will not provide emissions with a sufficient intensity to be detected, properly measured, and or quantified. In this latter case, it may be assumed that the test surface that was swabbed was relatively free of analyte being tested or checked for.

To assure a clear understanding of the description of the present invention provided herein, it is helpful to establish a relationship of the first portion 32 and the first porous pad, with the second portion 40 and the second porous pad. The first portion 32 will be defined as the portion that is coupled or fixed directly to the detector head housing 12 or 12a. Further, the first porous pad, which may be either a swabbing pad 54 or a porous pad 68, is fixed to the first portion 32. Similarly, the second portion 40 is structured to be mated to the first portion 32 to form the light-tight environment, and has fixed thereto a second porous pad. Again, the second porous pad may be either a porous pad 68 or a swabbing pad 54, which ever is needed to mate to the first porous pad.

In accordance with the present invention, a preferred method of examining a test surface is realized by swabbing the surface in order to collect and subsequently quantitatively indicate the presence of analyte. It must be noted that the methods of the invention may be realized with the exemplary structures and arrangements provided herein, as well as other structures providable by skilled individuals who have carefully reviewed the content of this disclosure. The methods of the present invention may involve several preliminary steps, such as installing the detector cap assembly 30 upon the detector head assembly 12, calibrating the luminometer, as well as other possible initial steps. Next, as shown in FIG. 2, a first porous pad, such as swabbing pad 54, is exposed. A user may then swab one or more selected test surfaces by contacting the first surface 54a of a pre-wetted swabbing pad 54. As discussed, the (porous) swabbing pad 54 may be structured with the first surface 54a shaped and configured for contacting the test surface to collect portions of available analyte.

After one or more test surfaces have been swabbed in an attempt to collect analyte upon the first surface 54a of the swabbing pad 54, the light-tight environment is re-established when the second portion 40 of the detector cap assembly 30 is re-installed over the first portion 32. At that point both the first porous pad and the second porous pad are shielded from ambient/external lighting sources (as depicted in FIGS. 3 and 4B). Next, or possibly in the process of replacing the second portion 40, the first surface 54a of the pre-wetted swabbing pad 54 is placed or brought into pressure contact with the reagent impregnated porous pad 68. The pressure contacting is realized, for example, by the moving of the movable portion 68 from a first retracted position (as depicted in FIG. 4A) to a second deployed position (as depicted in FIG. 4B). This may be accomplished with the illustrated structure, or any other arrangement that enables the desired pressure contacting to occur after swabbing. As indicated above, the pressure contacting results in the wetting of the dried reagents within and or upon the porous pad 68, causing the reagents to dissolve and be drawn from the porous pad 68 to the swabbing pad 54. If suitable quantities of analyte have been collected from the test surface, a detectable low level luminescent assaying reaction may be efficiently detected and quantified.

In preferred embodiments of the invention, when the first porous pad is brought into pressure contact with a suitably shaped second porous pad, the first surface 54a of a swabbing pad 54 and the second surface 54b thereof are compressed with the distance between at least one portion of the first surface 54a and the second surface 54b being substantially reduced with said pressure contacting. This will clearly result in a better wetting of the porous pad 68. In addition, such a compression of the swabbing pad 54 may importantly provide for an even more efficient detecting of any emitted low level luminescent emissions, with the detecting realized by a detection means that is efficiently (e.g., closely) positioned proximate to the second surface 54b of the first porous pad. It may be noted that the term 'sufficiently reduced', as applied above to the compression of the swabbing pad, may be assumed to indicate that the distance between at least a portion of the first surface 54a and the second surface 54b of the swabbing pad 54 is reduced by at least 15% to 70% of the uncompressed distance therebetween.

An important characteristic of preferred embodiments of the present invention is the use of a swabbing structure wherein swabbing and collecting of analyte occurs on a first side or surface (e.g., first surface 54a of the swabbing pad 54), with detectable low level luminescent emissions emitted from a second side or surface (e.g., second surface 54b). The emitted luminescent emissions may then be coupled to, and efficiently detected by, a suitable photo-detecting means. As can be seen in FIG. 4B, the pressure contacting of the swabbing pad 54 and the porous pad 68 occurs within close proximity of a photodiode 124—providing for a truly efficient detection arrangement in accordance with the present invention.

It is also important to note that items such as the first porous pad and the second porous pad, as well as others porous pads and related structures, may most preferably be formed of a material having bright, reflective color, and a porosity or "openness" of 60% to 95%. Accordingly, porous polymer pads and more generally porous polymeric materials, would provide an example of a most preferred material having a bright reflective coloring and a sufficient openness suitable for use with the present invention. The use of bright and open materials is helpful for several reasons. First, the openness enables a pre-wetted porous pad, such as swabbing pad 54, to absorb and retain a sufficient volume of wetting agent utilized for both swabbing and pressure contacting purposes. In addition, an assaying reaction producing low level luminescent emissions may be easily supported thereupon. A most interesting consequence of the use of porous pads having the above characteristics is that any assaying reaction produced thereupon, results in luminescent emissions being reflected, channeled, and therefore transmitted to other portions or areas of the included porous pad(s). As such, it may be said that a reflective coloring and open/porous structure of these items 'enhances' the ability to detect and quantify the luminescent emissions produced by a reaction occurring thereupon.

Figure 9:
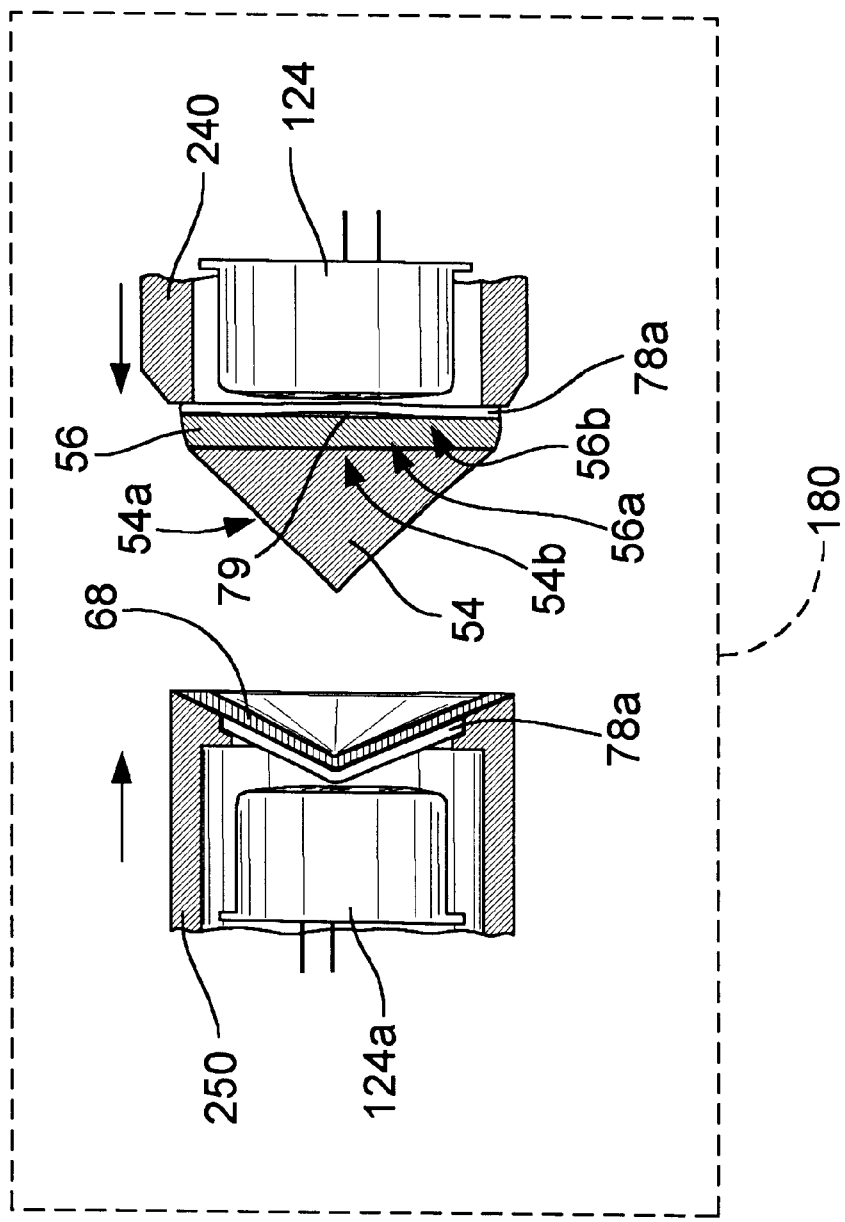
FIG. 9 depicts an arrangement of important elements of a most preferred embodiment of an analyte collection and assaying means in accordance with the invention.

It may also be assumed that emitted photons of the luminescent emissions, which are produced by the assaying reaction, may reach (a sensing portion of) the photodiode 124 or an equivalent means by at least one or more of the following mechanisms: (1) directly from the swabbing pad 54, or another pad superposed over the window 14, (2) indirectly via reflected luminescent emissions (say produced on or near the porous pad 68), and (3) emissions produced by a liquid phase or layer. For completeness, each type of emission delivery mechanism will be briefly discussed. It should be noted that the definitions and descriptions of these terms may be extended and or applied to other, possibly quite different structures. Direct emissions are emissions associated with a portion of an assaying reaction that is occurring quite close to, if not upon, a second surface of a first porous pad closest to a photo-detecting means. Indirect (reflected) emissions are luminescent emissions that are produced in more distant portions of the assaying reaction. For example, a portion of the reaction occurring near or on the second porous pad. These more distantly produced emissions are reflected and transmitted via a reflective coloration, and the openness of the employed porous pads of the invention. A term that may be used to describe the inherent mechanism (of the employed porous pads) to deliver indirect emissions is 'reflective porosity'. Finally, liquid phase emissions are emissions that may occur or are caused to occur in a layer of liquid situated between a second surface (e.g. 54b of the swabbing pad 54) of a porous pad and an included moisture barrier 78 or 78a. This liquid may be composed of, or include, wetting agent, analyte, and reagents. As shown in FIG. 9, liquid phase emissions may be encouraged by providing a small pocket 79 between an adjacent porous pad 56 and a second (moisture) barrier 78a. It is the above emission delivery mechanisms, and equivalents, in combination with the swabbing structures of the present invention, that provide the unexpected result of being able to accurately detect and quantify low level luminescent emissions of an assaying reaction using means based on inexpensive semiconductor photodiode detectors (as opposed to more sensitive and costly PMT based luminometer devices).

Skilled individuals will appreciate the need to prevent moisture and humidity from prematurely activating the dried reagents of a reagent impregnated porous pad, such as porous pad 68 of FIG. 4A. If the detector cap assembly 30 (including the porous pad 68) is packaged in a suitable packaging arrangement, then moisture and humidity may be blocked by such a packaging. Alternately, a means may be provided to seal the internal chamber 48 until such a time that the movable structure 64 is to be moved from the first retracted position (FIG. 4A) to the second deployed position (FIG. 4B). Also, a sealing means must be arranged to enable the suitable wetting of the porous pad 68 when the pressure contacting of the swabbing pad 54 and porous pad 68 occurs. Such a sealing or barrier means may be provided by a first moisture barrier 70, which may be structured to be thin and frangible (for the present embodiment). The moisture barrier 70 is arranged to cover the opening 52 (FIG. 2) of the second portion 40, preferably in a recessed fashion, as illustrated is FIG. 4A. A support ring 70a may further be provided to support a frangible embodiment of moisture barrier 70, as illustrated. The arranging of the moisture barrier 70 in the recessed fashion enables a portion of an internal chamber 48 having the porous pad 68 and the movable structure 64 contained therein to be hermetically sealed while the movable structure 64 is in the first (retracted) position. As such, the hermetically sealed portion of the internal chamber 48 enables the porous pad 68 to remain dry (while the movable structure 64 is maintained in the first retracted position). The recessed positioning the moisture barrier 70 will also enable the detector head assembly and the first portion 32 to be placed (coextensively) into the second portion 40 without rupturing the moisture barrier 70. Accordingly, after swabbing has been completed, possibly causing analyte to be collected upon the swabbing pad 54, the second portion 40 may be re-installed over the first portion 32. The movable structure 64, including the porous pad 68, may next be moved from the first retracted position (FIG. 4A) to the second deployed position (FIG. 4B), causing the moisture barrier 70 to be ruptured.

It should be noted that frangible embodiments of the moisture barrier 70 must be structured to be appropriately ruptured when the movable structure 64 is moved from the first retracted position to the second deployed position. The term 'appropriately rupturing' (and equivalents) may be defined as rupturing in a suitable fashion so as to enable sufficient wetting agents of the swabbing pad 54 to wet the dried reagents of the porous pad 68 and cause a desired assaying reaction (when sufficient analyte is present). As such, a suitable moisture barrier 70 may be scored with score lines (not shown) that are provided to establish rupture or tear locations to facilitate the appropriate rupturing of the moisture barrier 70. Further, if the moisture barrier 70 is provided by a stretched, possibly elastic material, the rupturing may result in a maximal direct contacting of the swabbing pad 54 and the porous pad 68 when the pressure contacting is established.

As illustrated in FIGS. 4A and 4B, a transparent supporting and fluid impervious second barrier 78 may be provided under the first porous pad (i.e., swabbing pad 54) and over the second opening 34b of the first portion 32. The second barrier 78 may be included to seal the second opening 34b to prevent the transport of items such as moisture, analyte, reagents, contaminants, etc., therethrough. There are at least two situations where such a transport may occur. First, when the detector cap assembly 30 is not installed over the head assembly 12 of the detector head housing 20a, moisture may pass through the first opening 34a of the first portion 32 and possibly contaminate the first porous pad. Alternately, when the movable structure 64 is moved to the deployed position (as shown in FIG. 4B), it is desirable to prevent the transport and loss of any of the wetting agent through the second opening 34b of the first portion 32. Therefore, should the second barrier 78 be omitted, the transport and loss of wetting agent may be controlled by the window 14 of the detector head assembly 12. However, as skilled persons would appreciate, the inclusion of the moisture barrier 78 prevents any contaminants, analyte, and or other matter from passing from the swabbing pad 54 to the detector head assembly 12 or visa-versa.

Primary purposes for employing a (volume of) wetting agent is to enable analyte to be easily collected, while also providing a means to wet and activate the dried reagents of the porous pad 68. When considering appropriate wetting agents to employ, a volume of sterile water, a nucleotide releasing reagent, and or a variety of other known buffering agents may be used. The particular wetting agent may actually be determined by skilled persons as a function of the particular analyte to be detected or assayed, as well as the particular dried reagents employed with the porous pad 68. Preferred materials suitable for providing the swabbing pad 54 include well known porous substances such as polymer pad materials, and or cotton. However, it should be noted that any substance which enables a sufficient volume of the wetting agent (say for example 0.1 ml to 1 ml) to be absorbed, and further enable the analyte to be collected during swabbing activities, may be employed. Similarly, when considering materials that may be employed to provide the porous pad 68 a number of known materials will suffice. However, a preferred structure contemplated to embody the porous pad 68 includes one or more layers of a (possibly paper) blotter material, a thin sponge-like material, and or one or more layers of a porous polymer sheet material.

When considering the structure of a means to move the movable portion 64 from the retracted position (FIG. 4A) to the deployed position (FIG. 4B) while enclosed or contained in the light-tight environment, it must be noted that any suitable structure that enables such a movement to be realized by a user, is contemplated as being within the scope of the present invention. For example, the embodiment of the detector cap assembly 30 as illustrated in FIGS. 4A and 4B provides one of many possible structures that may be employed. Other suitable structures may certainly be provided by skilled persons.

As shown in FIGS. 4A and 4B, the detector cap assembly 30 is arranged with the second portion 40 comprising of an outer cap-like portion 80 having a preferably cylindrical wall structure 82 that is closed by a top surface 84 at a second end 82b. The first end 82a of the wall structure 82 of the cap-like portion 80 is open. The wall structure 82 is arranged with a threaded portion 86a that is provided on an interior surface 86 thereof. As shown in FIGS. 4A and 4B, the threaded portion 86a of the interior surface 86 may most preferably begin proximate to the second (closed) end 82b and extend a suitable distance (e.g., approximately halfway or so) down the height of the cap-like portion 80 along the interior surface 86. As shown, the second portion 40 of the embodiment of FIGS. 4A and 4B is further arranged having a wall structure 42, and a first end 42a and a second end 42b. An outer surface 46 of the wall structure 42 of the second portion 40 is configured with a treaded portion 46a that is structured to mate to and engage the threaded portion 86a of the interior surface 86 of the outer cap-like portion 80. The respective engaged threaded portions thereby enabling the outer cap-like portion 80 to move along a common center or longitudinal axis of the second portion 40 (and the outer cap-like portion 80) when the outer cap-like portion 80 is rotated about the center axis with respect to the second portion 40. This rotation effectively causes the outer cap-like portion 80 to be screwed coaxially and (at least partially) coextensively down and over the second portion 40, moving the movable portion 64 (or an equivalent structure supporting the porous pad 68) from the retracted position to the deployed position. As is shown in FIGS. 4A and 4B, the movable structure 64 may be fixed directly to the top surface 84 of the outer cap-like portion 80, extending down into the second portion 40 as shown. As discussed above, the movement of the movable structure 64 to the second deployed position may cause a frangible moisture barrier 70 (if included) to be ruptured, and effect the placement of the porous pad 68 in pressure contact with the swabbing pad 54.

Referring now to FIGS. 5 through 8, there is illustrated another possible embodiment of the present invention. As clearly shown, a detector cap assembly 130 may include a first portion 132, a second portion 140, and a spacer 160. As with earlier embodiments, the first portion 132 is structured to mate (e.g., via a friction-fit) with a detector head assembly 12a, which as illustrated may be configured as a female detector head portion 12a. Accordingly, the first portion 132 of the detector head assembly 130 is structured to be inserted into a portion of the detector head housing 20b, as shown in FIGS. 6A and 6B. A transparent window 14 of this alternate embodiment is recessed from the opening of the detector head assembly 12a, as can be best seen in FIGS. 7B and 7C.

Figure 7B:
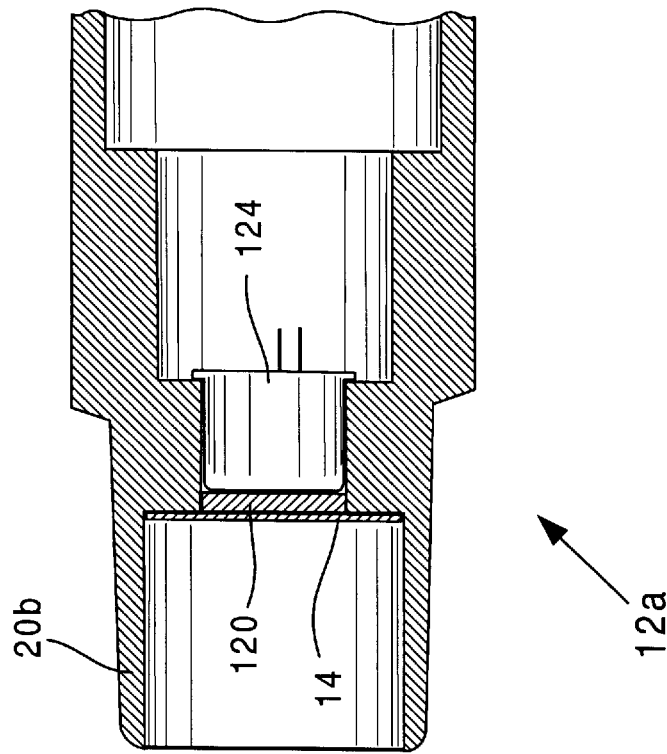
FIGS. 7A and 7B provide sectional side views of an embodiment of the detector cap assembly and a detector head assembly, taken along the lines 7A—7A and 7B—7B of FIG. 5, which are consistent with the embodiment of FIGS. 5, 6A and 6B.
Figure 7A:
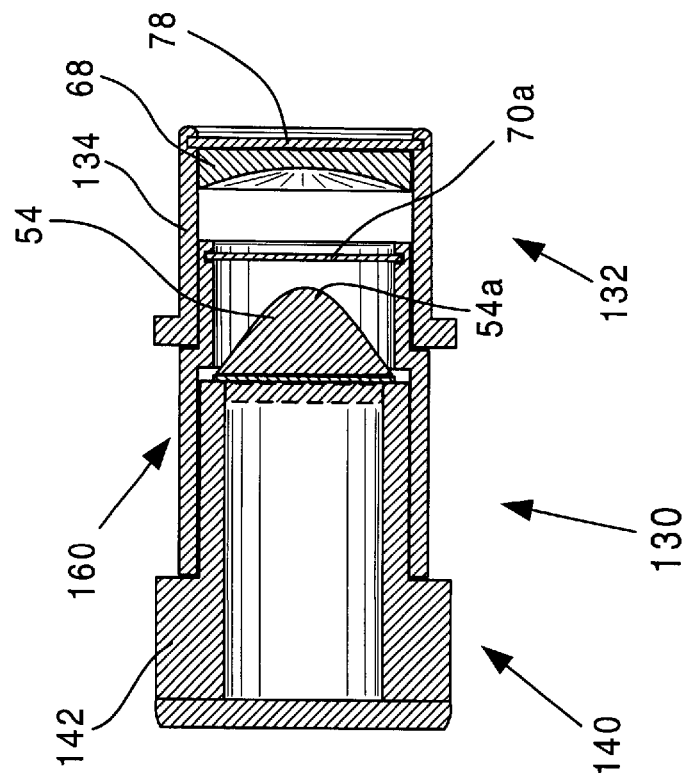
Figure 7C:
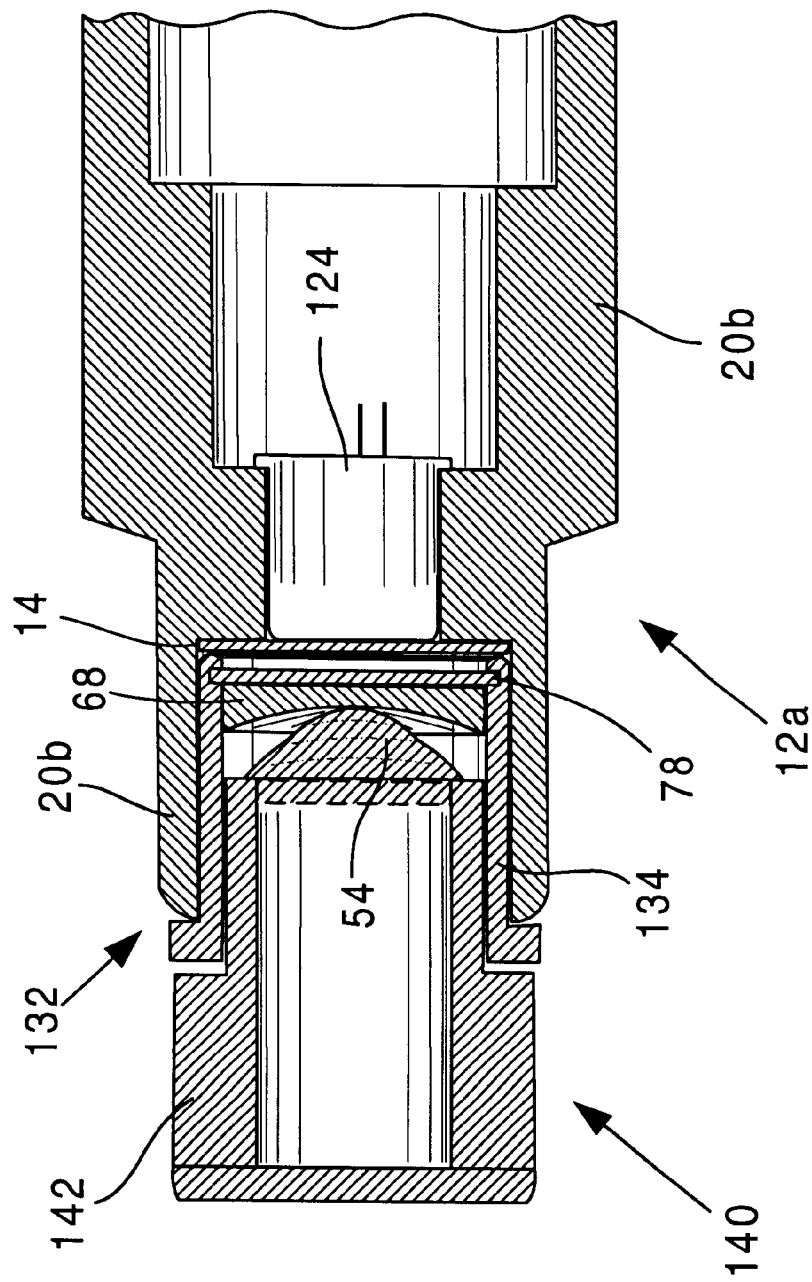
FIG. 7C provides sectional side view of the detector cap assembly of FIG. 7A mated to the detector head assembly of FIG. 7B, after a spacer portion has been removed.

As with earlier embodiments of the invention, the structure of this alternate embodiment places a porous pad, as shown in FIG. 7C, in close proximity to the photo-detection means, such as a semiconductor photodetector 124. Again, this arrangement, wherein a porous pad (say, either swabbing pad 54 or porous pad 68) is situated proximate to and superposed over a photo-detection means of a suitable luminometer, enables the efficient detecting and quantifying of low level luminescent emissions emitted, at least in part, from one or more porous pads.

Figure 6A:
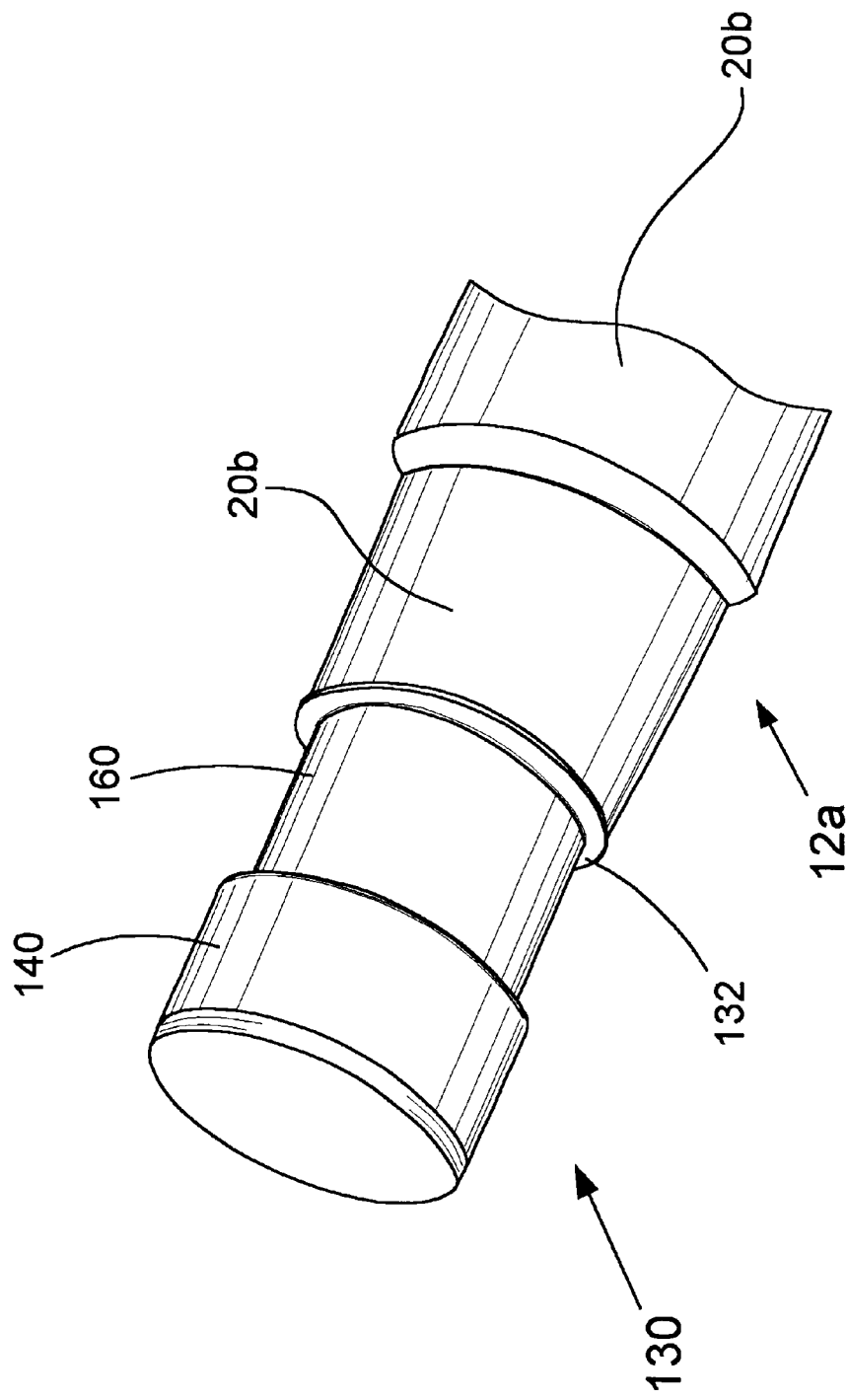
FIG. 6A shows the detector cap assembly of FIG. 5 installed upon (or removably fixed to) the detector head assembly of FIG. 5.
Figure 6B:
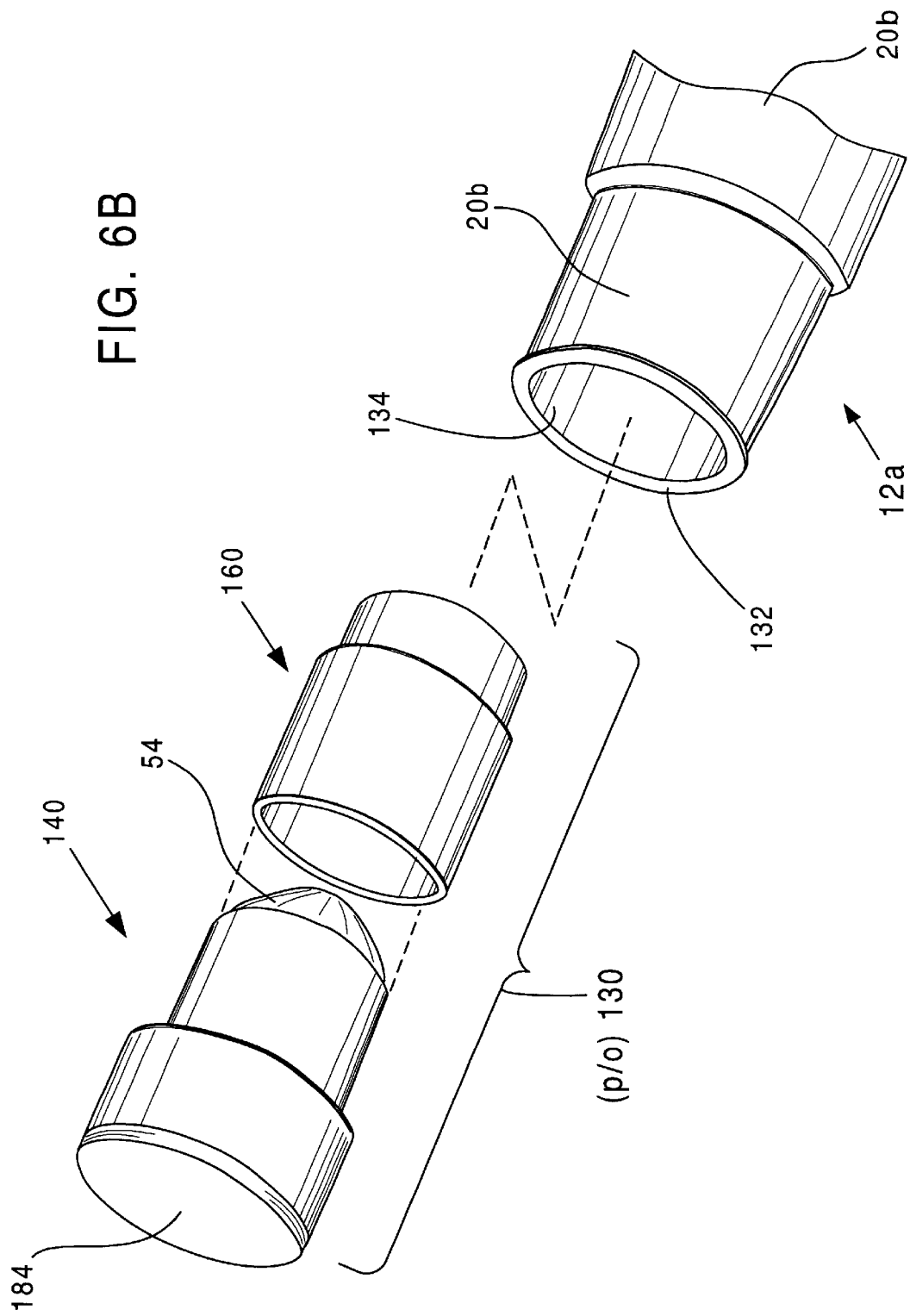
FIG. 6B depicts the detector cap assembly of FIGS. 5 and 6A with a second portion and a spacer shown separated from a first portion thereof.

Returning to FIG. 6A, once the detector cap assembly 130 is fixed to the detector head assembly 12a, the second portion 140 and the spacer 160 may be detached or separated from the first portion 132. Once the second portion 140 is separated from the spacer 160, as can be seen in FIG. 6B, a swabbing pad 54 (i.e., a second porous pad) that is fixed to the second portion 140 is available to swab a test surface and possibly collect analyte therefrom. The second portion 140 would then be mated directly to the first portion 132 (which is installed on the detector head assembly 12a). As can be seen in FIG. 7C, when the first portion and second portion are mated directly to each other, a pressure contacting occurs between the swabbing pad 54 of the second portion 140 and the porous pad 68 of the first portion 132. As with earlier embodiments, this may result in an assaying reaction producing low-level luminescent emissions that may be detected and quantified in accordance with the present invention. As discussed above, since the swabbing pad 54 is fixed to the second portion 140, the swabbing pad 54 of this embodiment, may be termed a 'second porous pad' (as it is fixed to the second portion). Similarly, the porous pad 68 of this embodiment may be termed 'a first porous pad'.

Referring to FIGS. 7A and 7B, illustrated therein are sectional side views of an embodiment of the detector cap assembly 130 and a detector head assembly 12a, taken along the lines 7A—7A and 7B—7B, respectively, of FIG. 5. These sectional views are consistent with the embodiment of FIGS. 5, 6A, and 6B, and as such are representative of one possible internal structure that may be utilized with this embodiment. As can be seen in FIG. 7A, the first portion 132 is structured to support a porous pad 68 (impregnated with dried reagents). As illustrated, the porous pad 68, which may be termed a first porous pad, may preferably be supported at the beginning of the first portion 132, which first enters the detector head housing 20b. As depicted in FIG. 7A, the porous pad 68 may be provided with a somewhat concaved shape. The spacer 160 is structured to be interposed between and suitably mated to the first portion 132 and the second portion 140. As such, the spacer is included to provide for the suitable long term storage of a detector cap assembly 130, while maintaining a required separation between the first and second porous pads until the swabbing of a test surface is desired. As illustrated, a (first) moisture barrier 70a is included within the spacer 160. As skilled persons will appreciate, it is the combination of the moisture barrier 70a and a second barrier 78 of the first portion that may be configured to provide a desired hermetic seal of the porous pad 68 to prevent moisture, contaminates, etc., from reaching the porous pad 68 before it is intended for use in pressure contacting with the swabbing pad 54. In a like fashion, when the second portion 140 is removably fixed to the spacer 160, as illustrated in FIG. 7A, the swabbing pad 54 may be contained in a sealed environment, preventing wetting agents that are employed to pre-wet the swabbing pad 54 from evaporating and or being contaminated.

A possible advantage of the embodiments depicted in FIGS. 5 through 7C, is a much simpler arrangement to package the detector cap assembly 130, as well as a much simpler structure to enable a user to swab a test surface and cause the pressure contacting of the first porous pad (here porous pad 68) with the second porous pad (swabbing pad 54) within a suitable light-tight environment. As with earlier embodiments, the pressure contacting possibly resulting in an assaying reaction producing detectable low level luminescent emissions that may be detected and quantified by the luminometer.

Figure 8:
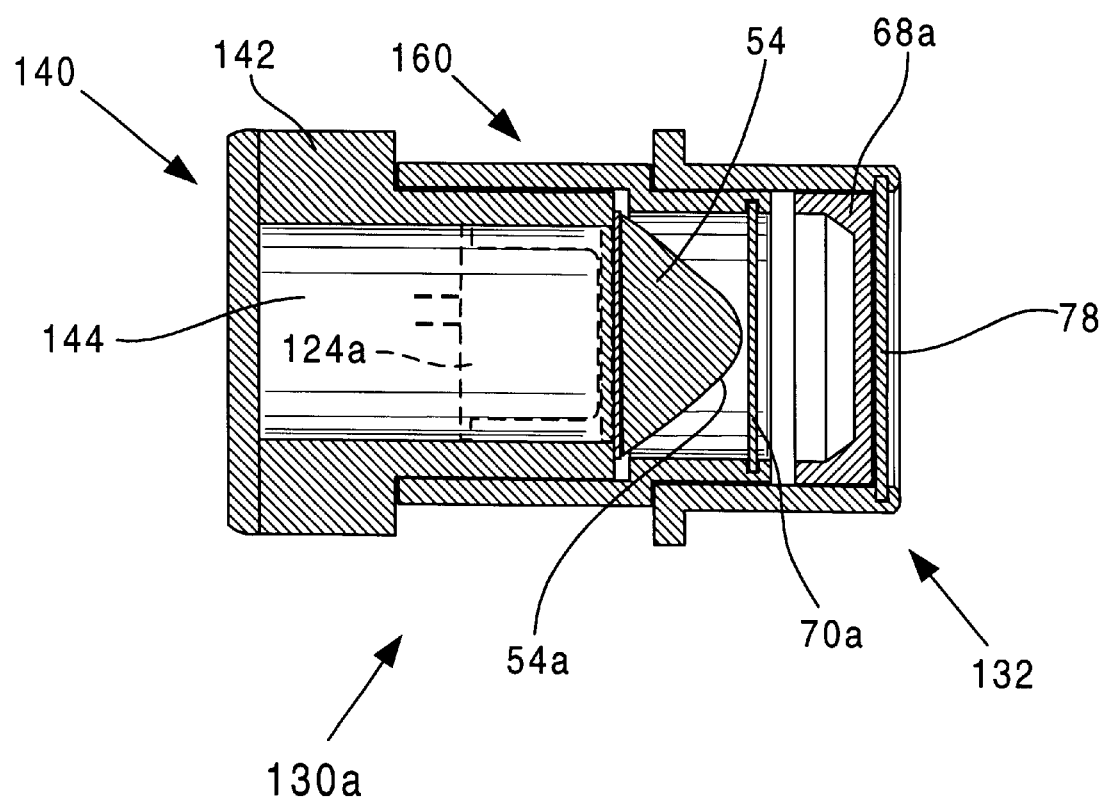
FIG. 8 provides a sectional side view of yet another possible embodiment of a detector cap assembly.

Yet another embodiment of the detector cap assembly 130a is illustrated in FIG. 8. This embodiment may provide several additions to earlier embodiments of the detector cap assembly. First, as skilled persons would appreciate, the efficiency of the detecting of low level luminescent emissions may be enhanced further by including at least one additional photo-detection means. As shown in dotted lines, a second semiconductor photodiode 124a may be included within an internal cavity 144 the second portion 140. As illustrated the semiconductor photodiode 124a may be situated proximate to and superposed by the second porous pad provided by swabbing pad 54, which enables the efficient detecting and quantifying of available low level luminescent emissions emitted therefrom. Accordingly, the embodiment of FIG. 8, may enable the sensing of luminescent emissions emitted from a each of the noncontacting sides of the first and second porous pads. Also shown in FIG. 8 is a modified porous pad 68a, which is structured having a deeper concave or what may be termed a 'deep concaved shape'. For example, a preferred concave may provide for a concaved depth of that is 5% to 30% (or more) of the diameter of the first porous pad.

As skilled persons will understand, the embodiments of the detector cap assemblies 30 and 130/130a are exemplary of many such possible arrangements and structures. Accordingly, it is possible to provide yet other structures employing a swabbing pad 54 and a porous (reagent impregnated) pad 68 in accordance with the present invention.

Returning again to FIG. 7B, an electronic shutter 120 may also be provided within detector head housing 20/20a of the detector head assembly 12. The electronic shutter 120, when included, is preferably superposed over and abutting the semiconductor photodiode 124 and immediately below or behind the transparent window 14 (as shown in FIG. 7B). Importantly, the window 14 of the detector head housing 20b is the only avenue for luminescent emissions to be incident upon and detected by the photodiode 124. The electronic shutter 120 is configured to be set to one of either a darkened state thereby significantly restricting the level of luminescent emissions incident upon the photodiode 124 and a nearly transparent state enabling available luminescent emissions to reach and be detected by the photodiode 124. The term 'significantly restricting', as applied to the level of emissions reaching the photodiode 124 when the electronic shutter 120 is in the darkened state, may be assumed to indicate that the level of emissions reaching and detected by the photodiode 124 may be reduced to a level of $\frac{1}{100}$th to $\frac{1}{1000}$th of the level incident when the electronic shutter 120 is in the nearly transparent state. The capability to significantly reduce the level of emissions reaching the photodiode 124 is desirable for a number of reasons. First, as a luminometer suitable for use with the invention is constructed to be sensitive to low levels of emissions, exposure to the relatively high levels of common ambient room lighting may saturate or even damage electronic circuits included therewith. Accordingly, when the detector cap assembly is not installed over the detector head assembly 12 (or the second portion 140 and spacer 160 are removed or separated from the first portion 132), it is desirable to set the electronic shutter 120 to the darkened state. Other functions of an electronic shutter 120, if included, will be fully understood by skilled persons.

Although a mechanical shutter may be employed with the present invention, the use of electronic shutter 120 reduces the mechanical complexity and the cost of construction for preferred embodiments of the detector head assembly 12/12a. A most preferred version of the electronic shutter 120 may be provided by a polarizing liquid crystal shutter, also known as an LCD shutter. By including suitable electronic couplings (e.g., electrical conductors and connectors), circuitry of a suitable luminometer may be employed to control one or more included the electronic shutters 120. Further, in order to not obfuscate the essential functional and operational characteristics of the various embodiments of the invention as illustrated, certain required and known items and or structures have been omitted. For example, in FIGS. 4B and 7B electrical couplings from the semiconductor photodiode 124 have been omitted. Similarly, the electrical couplings required for semiconductor photodiode 124a, if included, have been omitted. These items may be readily provided by skilled individuals.

An important feature of the present invention, which is clearly shown in FIG. 9, may be associated with a core structure that is employed with many embodiments of the present invention. It should be noted that not every structure illustrated in FIG. 9 is required for each possible embodiment contemplated. As can be seen a swabbing pad 54 is coupled (either directly or via a support and reading pad 56) to a suitable wall or support structure 240. A photo-detection means, such as semiconductor photodiode 124, may be provided and situated for the efficient detecting of low level luminescent emissions emitted (directly or indirectly) from a second surface 54b of the swabbing pad 54. A second (opposing) structure provides a porous pad 68, which is suitably supported (as illustrated) by a wall or support structure 250. In addition, at least one other photo-detection means, such as semiconductor photodiode 124a, may be provided for the efficient detecting of low level luminescent emissions emitted directly from the porous pad 68. Importantly, as with other embodiments, the swabbing pad 54 and the porous pad 68 must be configured to be brought into pressure contact within a light-tight environment 180 (conceptually shown in a dotted line). Should the embodiment of FIG. 9 include both semiconductor photodiodes 124 and 124a, a most efficient and possibly most preferable detection of low level luminescent emissions may be realized. As skilled persons will understand, the configuration of the swabbing pad 54 and the porous pad 68, along with the needed support and wall structures, may be provided with embodiments similar to those of FIGS. 1 through 5, FIGS. 6A through 8, or yet other possible arrangements. Accordingly, the structure of FIG. 9 may be assumed to be define a preferred embodiment of a central portion the present invention in a broad and functional form.

Turning again to FIG. 9, yet another feature of the present invention is shown. As depicted a preferably substantially flattened support and reading pad 56 having a first surface 56a may be fixed to the second surface 54b of the swabbing pad 54 (or equivalently, and not illustrated, to the porous pad 68). The support and reading pad 56 would most preferably be provided by a material having a bright, reflective coloring, and a high porosity or openness of approximately 80% to 95%. The first surface 56a of the support and reading pad 56 may be said to be superposed by the second surface 54b of the swabbing pad 54, as shown in FIG. 9. As discussed above, a first portion such as first portion 32 may be structured with a wall portion 34 and a second (transparent) barrier 78, which may be considered a means to support the support and reading pad 56, and therefore indirectly the swabbing pad 54. The structure of FIG. 9 is specifically contemplated to enable the swabbing of a test surface and subsequently facilitate the detecting, in a light-tight environment, of any low level luminescent emissions emitted, at minimum, from a second side 56b of support and reading pad 56. This is similar to the function of previous embodiments, with the exception that the direct detecting of luminescent emissions of previous embodiments was made from the second surface 54b of the swabbing pad 54 or the second (inner) surface of the porous pad 68, instead of the second surface 56b of the support and reading pad 56.

The inclusion of the support and reading pad 56, as depicted in FIG. 9, may provide several functional improvements. First, the support and reading pad 56 may be formed of a material having an increased openness, yet may further be embodied to be stiffer (or firmer) than the material utilized to provide the swabbing pad 54. As such, when the pressure contacting of the porous pad 68 occurs, at least a portion of the wetting agent solution (including reagents and analyte) is absorbed by and moved into the support and reading pad 56. Therefore, the swabbing structure of FIG. 9 may provide for an improved ability to detect and quantify the luminescent emissions of the assaying reaction, primarily due to an increased portion of the assaying reaction possibly occurring in a very porous, firm, and reflectively colored support and reading pad 56. The support and reading pad 56 may be said to have a high 'reflective porosity', preferably greater than of equal to the swabbing pad 54 and the porous pad 68.

Another important feature of the present invention is also shown, in an exemplary fashion, in FIG. 9. The embodiment of a second barrier 78a may be provided having a small pocket 79 formed between the second surface 56a of the support and reading pad 56 and the barrier 78a. As discussed above, this pocket, may be useful in enhancing the emissions generated and transmitted directly to the photodiode 124 by a liquid phase (or layer) situated in the pocket 79 while the swabbing pad 54 is compressed. It may be noted that the pocket 79 may be provided with any of the embodiments of the present invention, regardless of weather the support and reading pad 56 is actually included.

While there have been described a plurality of the currently preferred embodiments of the present invention, along with varied methods of operation, those skilled in the art will recognize that other and further modifications may be made without departing from the invention, and it is intended to claim all modifications and variations as fall within the scope of the described invention and the appended claims.

What is claimed is:

1. An analyte collection and assaying assembly, comprising:

(a) a first porous pad fixed to a first portion of the assembly, the first portion structured to be removably fixed to a luminometer so that a second surface of the first porous pad is situated proximate to and superposed over a photo-detection means of the luminometer for detecting and quantifying low level luminescent emissions emitted, at least in part, from the first porous pad; and (b) a second porous pad fixed to a second portion of the assembly, the second portion structured to be removably fixed to the first portion after a test surface has been swabbed so as to form an internal light-tight environment that houses each of the first porous pad and the second porous pad;

(c) the assembly structured to bring the first porous pad into pressure contact with the second porous pad within the light-tight environment after a test surface has been swabbed with one of either the first porous pad and the second porous pad, the pressure contacting possibly resulting in an assaying reaction producing detectable low level luminescent emissions that may be detected and quantified by the luminometer.

2. The assembly in accordance with claim 1, wherein the first porous pad of the first portion is provided by one of:
  (a) a pre-wetted swabbing pad having a first surface and a second surface, with the first surface structured to swab a test surface after the first portion is separated from the second portion; and
  (b) a porous pad impregnated with dried reagents, the porous pad arranged for pressure contacting a pre-wetted swabbing pad after the swabbing pad has been employed for swabbing a test surface, the pressure contacting of the porous pad and a swabbing pad causing the wetting and activating of the dried reagents.

3. The assembly in accordance with claim 2, wherein the first portion is structured with a porous pad having a concaved pressure contacting surface.

4. The assembly in accordance with claim 1, wherein the second porous pad of the second portion is provided by one of:
  (a) a porous pad impregnated with dried reagents that is arranged for pressure contacting a pre-wetted swabbing pad fixed to the first portion; and
  (b) a pre-wetted swabbing pad having a first surface and a second surface, with the first surface structured to swab a test surface when separated from the first portion;
  (c) with the assembly structured to bring a porous pad impregnated with dried reagents and a swabbing pad into pressure contact within the light-tight environment.

5. The assembly in accordance with claim 4, wherein each of the first portion and the second portion is structured having a cylindrical wall structure.

6. The assembly in accordance with claim 5, wherein the second porous pad is structured with a concaved pressure contacting surface.

7. The assembly in accordance with claim 5, wherein the first porous pad and the second porous pad are provided with each having a porosity in the range of 60 to 95 percent.

8. A detector cap assembly providing an internal light-tight environment for conducting a self-contained assay of analyte collected from a test surface, the detector cap assembly comprising:
  (a) a first portion having fixed thereto a first porous pad, the first portion removably fixable to a detector head assembly of a luminometer to enable the efficient detecting and quantifying of low level luminescent emissions being emitted, at least in part, from the first porous pad; and
  (b) a second portion having fixed thereto a second porous pad, the second portion configured to be removably fixed to the first portion to establish the light-tight environment housing the first porous pad and the second porous pad;
  (c) the first portion and the second portion structured to enable a user to bring the first porous pad into pressure contact with the second porous pad within the light-tight environment.

9. The detector cap assembly in accordance with claim 8, wherein the first porous pad of the first portion is a pre-wetted swabbing pad arranged to swab the test surface when separated from the second portion.

10. The detector cap assembly in accordance with claim 9, wherein the second porous pad is impregnated with dried reagents, with the pressure contacting of the swabbing pad and the second porous pad compressing the swabbing pad and causing the wetting and activating of the dried reagents of the second porous pad, possibly resulting in an assaying reaction producing the low level luminescent emissions.

11. The detector cap assembly in accordance with claim 10, wherein the first portion is structured to situate a second surface of the first porous pad proximate to and superposed over a photo-detection means of the detector head assembly to efficiently detect and quantify the low level luminescent emissions.

12. The detector cap assembly in accordance with claim 11, wherein the photo-detection means includes at least one semiconductor photodiode.

13. The detector cap assembly in accordance with claim 12, wherein the photo-detection means further includes at least one additional semiconductor photodiode located within the second portion, with each semiconductor photodiode situated proximate to and superposed by a surface of a porous pad.

14. The detector cap assembly in accordance with claim 8, wherein the first porous pad is impregnated with dried reagents and is fixed to the first portion so as to situate a second surface of the first porous pad proximate to and superposing a photo-detection means of the detector head assembly, to efficiently detect and quantify the low level luminescent emissions.

15. The detector cap assembly in accordance with claim 14, wherein the second porous pad of the second portion is a pre-wetted swabbing pad, the second portion structured to be separated from the first portion of the detector cap assembly to enable the swabbing of the test surface, and subsequently fixed again to the first portion, bringing the first porous pad into pressure contact with the second porous pad within the light-tight environment, and causing a wetting and activating of the dried reagents.

16. The detector cap assembly in accordance with claim 15, wherein each of the first porous pad and the second porous pad is situated with a respective surface proximate to and superposed over a photo-detection means to efficiently detect and quantify the low level luminescent emissions.

17. The detector cap assembly in accordance with claim 16, wherein the photo-detection means includes at least one semiconductor photodiode.

18. The detector cap assembly in accordance with claim 17, wherein the detector cap assembly further includes a spacer that is interposed between the first portion and the second portion to provide for suitable long term storage while maintaining a required separation between the first and second porous pads until swabbing of a test surface is to commence.

19. The detector cap assembly in accordance with claim 18, wherein the spacer includes a first barrier, with the spacer structured to mate with the second portion causing the swabbing pad to be hermetically sealed in an internal chamber.

\* \* \* \* \*